United States Patent [19]
Diebold et al.

[11] Patent Number: 5,437,999
[45] Date of Patent: Aug. 1, 1995

[54] ELECTROCHEMICAL SENSOR

[75] Inventors: Eric R. Diebold, Fishers; Richard J. Kordal, Zionsville; Nigel A. Surridge, Indianapolis; Christopher D. Wilsey, Carmel, all of Ind.

[73] Assignee: Boehringer Mannheim Corporation, Indianapolis, Ind.

[21] Appl. No.: 200,174

[22] Filed: Feb. 22, 1994

[51] Int. Cl.[6] .................. C12M 1/40; C12M 1/34
[52] U.S. Cl. ..................... 435/288; 435/291; 435/817; 422/82.01; 204/403
[58] Field of Search ............... 435/288, 291, 817; 422/82.01, 82.02; 204/400, 403, 434, 435, 153.12

[56] References Cited

U.S. PATENT DOCUMENTS

| | | | |
|---|---|---|---|
| 4,571,292 | 2/1986 | Liu et al. | 204/412 |
| 5,108,564 | 4/1992 | Szuminsky et al. | 204/153.12 |
| 5,108,819 | 4/1992 | Heller et al. | 428/195 |
| 5,141,868 | 8/1992 | Shanks et al. | 435/288 |
| 5,229,282 | 7/1993 | Yoshioka et al. | 435/177 |

FOREIGN PATENT DOCUMENTS

| | | | |
|---|---|---|---|
| 0127958B1 | 3/1992 | European Pat. Off. | G01N 33/48 |
| 62-85855 | 4/1987 | Japan | G01N 27/30 |
| 0129155 | 5/1989 | Japan | 204/403 |
| 2120655 | 5/1990 | Japan | 204/403 |
| 3-26956 | 2/1991 | Japan | G01N 27/416 |
| 5-72171 | 3/1993 | Japan | G01N 27/37 |
| 2073891 | 10/1981 | United Kingdom | G01N 27/28 |
| WO90/05300 | 5/1990 | WIPO | G01N 27/48 |
| WO90/05910 | 5/1990 | WIPO | G01N 27/26 |

OTHER PUBLICATIONS

Urban et al., "Miniaturized thin-film biosensors using covalently immobilized glucose oxidase", 1991, pp. 555–562, *Biosensors & Bioelectronics* 6.

Mastrototaro et al., "An electroenzymatic glucose sensor fabricated on a flexible substrate", 1991, pp. 139–144, *Sensors and Actuators* B.5.

Lindner et al., "Flexible (Kapton-based) Microsensor Arrays of High Stability for Cardiovascular Applications", 1993, pp. 361–367, *J. Chem. Soc. Faraday Trans.* 054382031 89(2).

National Science Foundation/Engineering Research Center for Emerging Cardiovascular Technologies, "Fifth Annual Report", 1993, pp. 41–42.

*Primary Examiner*—William H. Beisner
*Attorney, Agent, or Firm*—D. Michael Young; Max J. Kenemore; Marilyn L. Amick

[57] ABSTRACT

A method for fabricating high-resolution, biocompatible electrodes is disclosed, allowing production of an electrochemical sensor which is capable of precise analyte concentration determination on a very small sample size. Electrically conducting material is affixed to a first insulating substrate. A second insulating substrate is then affixed to the electrically conducting material and patterned using photolithography to define an electrode area. Alternatively, the electrically conducting material may be screen printed directly onto a standard printed circuit board substrate in the case of a counter or reference electrode. In either case, the substrate may be rigid or flexible. When the electrodes produced in accordance with the present invention are then used in an electrochemical sensor which includes a reagent, the small and highly-defined electrode areas permit highly-accurate electrochemical analyte measurements to be performed on very small sample sizes.

22 Claims, 5 Drawing Sheets

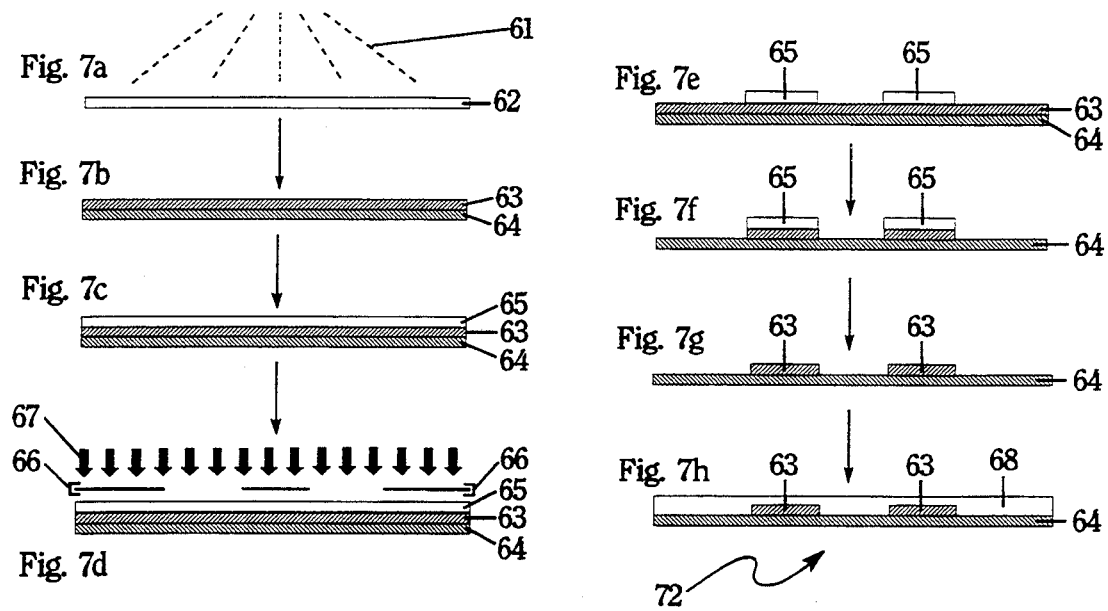
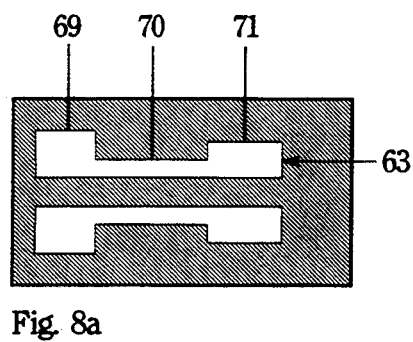
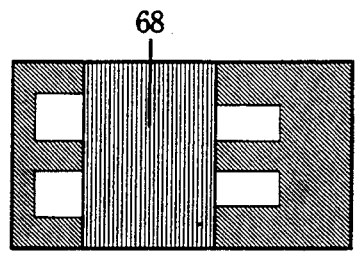

a
ELECTROCHEMICAL SENSOR

FIELD OF THE INVENTION

This invention relates to electrochemical sensors and to a process for fabricating electrodes for use in electrochemical sensors.

BACKGROUND OF THE INVENTION

The use of sensors in the medical field for testing various blood analytes and in the environmental field for monitoring water or soil contamination is well known. Many of these sensors perform an electrochemical measurement by applying a potential difference across two or more electrodes which are in contact with a reagent and sample. Two-electrode sensors are known which include a working electrode and either a counter or a reference/counter ("reference") electrode. Three-electrode sensors are also known which have a working electrode, a counter electrode, and a reference electrode. Since the area of the working electrode in any of the above sensor designs has a direct effect on the amount of current measured, it is highly desirable to fabricate sensors which have a precisely-defined working electrode area.

Fabricating electrodes for use in sensors has been accomplished by cutting and sealing, "thick-film" or "screen printing", and "thin-film" deposition methods (commonly used in the production of integrated circuits). Recently, photolithography has also been used to pattern electrodes on the surface of a substrate. While some of these techniques permit precise electrode sizing and placement on the support substrate, the ability of sensors made from such electrodes to make precise measurements is limited by the definition of the working electrode area.

Printed circuit boards ("PCBs") and flex circuits are widely used in the electronics industry as a means of interconnecting electrical components. There are two basic systems used to produce PCBs and flex circuits. One is called the "additive method" and the other is called the "subtractive method". With the additive method, the desired circuit pattern is built on top of a non-conductive plastic, ceramic, or other substrate. In the subtractive method, a non-conductive substrate (e.g., epoxy bonded fiberglass in the case of PCBs, polyimide in the case of flex-circuits) is laminated with a copper foil. The copper is then patterned using standard photolithography and wet chemical etching techniques. The copper circuit may subsequently be plated with nickel, gold, or other metal.

The metal patterning techniques described above which are common to the PCB industry, however, are unsuitable for biological applications (e.g., analyte sensing). The plating of metal onto a copper-clad substrate, as described above, results in an irregular, granular surface that allows penetration of a biological fluid to the underlying copper, thus giving rise to background electrochemical signals that interfere with measurements. In addition, copper and nickel are themselves electroactive at the potentials commonly used for sensing, and therefore cannot be used as a working electrode.

SUMMARY OF THE INVENTION

This invention is based on the novel adaptation of some techniques common to the PCB industry to produce high-resolution electrodes for use in an electrochemical sensor. The electrodes produced in accordance with the present invention have highly defined and reproducible size and shape, and importantly have a precisely-defined working electrode area. When the electrodes are then used in an electrochemical sensor, highly-accurate electrochemical measurements may be performed on very small sample sizes. A significant advantage to the present invention (when the sensor is used to detect or measure an analyte in a blood sample) is the low blood sample volume required for the electrochemical measurement, thus allowing for a very low pain lancet device which produces low sample volumes. Since in one embodiment the electrodes are manufactured on separate pieces of substrate material, another advantage of the present invention is the separation of the fabrication processes of the two electrodes, which allows separation of the chemistries associated with the working and the counter electrodes.

Fabricating an electrode in accordance with the present invention involves first attaching a high quality thin metal film (rather than copper foil laminates) to a bare rigid or flexible substrate. A layer of photoresist is then applied to the thin metal layer and patterned using photolithography to precisely define an electrode area and a contact pad. Importantly, the photoresist layer is not removed after patterning and acts as an insulator in the finished electrochemical sensor. Alternatively, a dielectric material may be screen printed directly to the metal layer in a pattern which defines the electrode area and contact pad. In the case of a reference or counter electrode, the metal may be applied directly to a standard PCB substrate.

The electrodes described above may then be used to fabricate a novel electrochemical sensor in which the electrodes are arranged either in opposing or adjacent form. When a reagent is applied to one or both exposed electrode areas, an electrochemical detection and/or measurement of an analyte in a sample may be performed.

BRIEF DESCRIPTION OF THE DRAWINGS

FIGS. 7a–7h show a method of fabricating adjacent electrode elements for use in an adjacent electrode electrochemical sensor in accordance with the present invention.

FIG. 8a shows a top view of FIG. 7g and FIG. 8b shows a top view of FIG. 7h.

DETAILED DESCRIPTION OF THE INVENTION

The adaptation of some PCB fabrication techniques to make electrodes functional in biological fluids relies on electrochemical inertness in the potential range of interest for sensing, approximately −1 to +1 volts versus silver/silver chloride (Ag/AgCl). In accordance with the present invention, high quality thin noble metal films are used as electrodes rather than copper foil laminates. These thin metal films can be sputtered or evaporatively deposited onto an appropriate foil material (e.g., polyester, polycarbonate, polyimide) and then laminated to a support substrate (e.g. by Courtaulds Performance Films, Canoga Park, Calif.). Alternatively, the thin metal films may be deposited directly onto the support substrate. The resulting metallized substrate displays extremely small and uniform grain size (10–50 nm (nanometers) diameter), and importantly does not contain copper or other electrochemically active materials. Such surfaces are nearly ideal for the purpose of making electrochemical measurements in biological or corrosive solutions. A second insulating substrate is then applied to the metal layer and precisely patterned to form an open electrode area and a meter contact pad. The combination of first insulating substrate, metal, and second insulating substrate is referred to herein as an "electrode element."

Two types of electrode elements are described below. The "opposing" electrode element is designed to be used in combination with a second opposing electrode element, separated by a spacer in a "sandwich" fashion. This embodiment is referred to as the "opposing electrode electrochemical sensor." The opposing electrode electrochemical sensor includes a working electrode element and either a counter or a reference electrode element as described below. The "adjacent" electrode elements are fabricated on the same substrate side-by-side in a parallel fashion. This embodiment is referred to as the "adjacent electrode electrochemical sensor." The adjacent electrode electrochemical sensor may include a working electrode element and either a counter or a reference electrode element, or may include a working, counter and reference electrode element.

FABRICATION OF OPPOSING ELECTRODE ELEMENTS FOR THE OPPOSING ELECTRODE ELECTROCHEMICAL SENSOR

Figure 1:
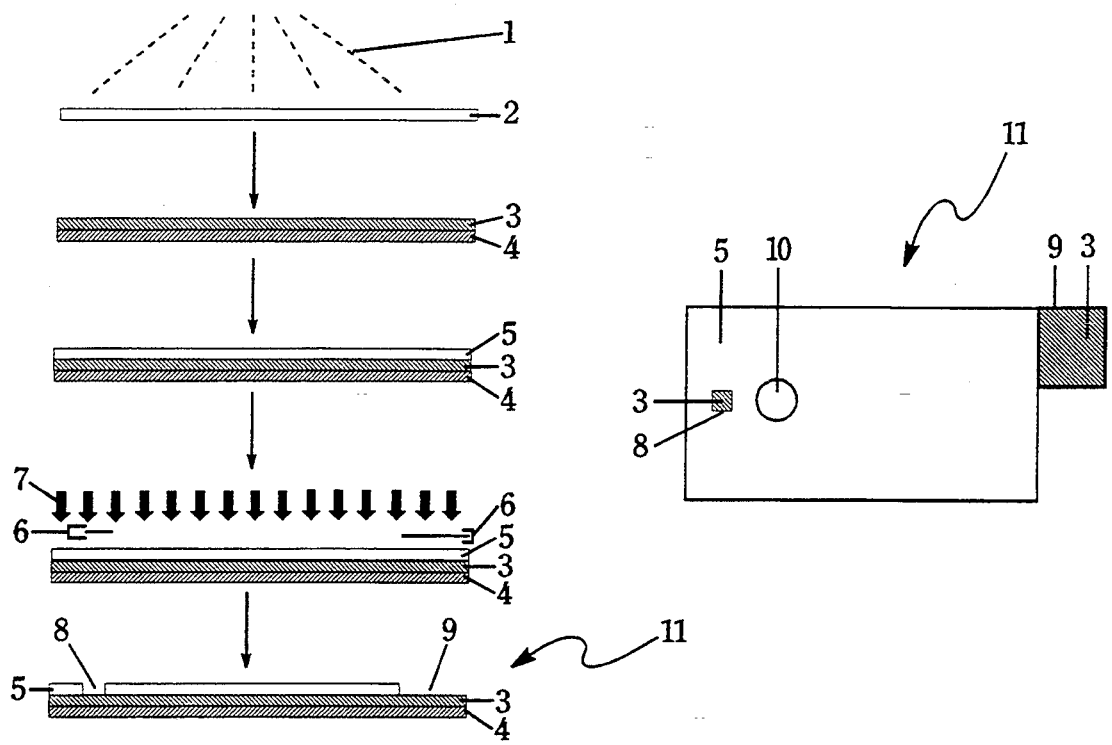
FIG. 1 shows a method of fabricating a working, counter, or reference electrode element in accordance with the present invention.

A working, counter, or reference electrode element may be produced in accordance with the present invention as shown in FIG. 1. Electrically conducting material 1 (e.g., a noble metal or carbon) is vacuum sputtered or evaporatively deposited onto thin support material 2 (e.g., polyimide or other polymer such as polyester, polyethylene terephthalate (PET), or polycarbonate) to form metallized thin support material 3 (e.g., by Courtaulds Performance Films, Canoga Park, Calif.). This step may or may not be preceded by depositing, with the same means, a thin anchor layer of chromium, titanium, or other suitable material (not shown in FIG. 1). The purpose of the thin anchor layer is to increase adhesion between electrically conducting material 1 and thin support material 2, as well as to stabilize the microstructure of electrically conducting material 1.

Alternatively, electrically conducting material 1 can be deposited onto the surface of thin support material 2 by the method of electroless plating or a combination of activation and electroplating. These processes are well known but will be briefly described. With electroless plating, thin support material 2 is cleaned and if necessary subjected to a surface roughening step. The surface of thin support material 2 is then chemically treated or "activated" with a colloidal catalyst (e.g., $PdCl_2$—$SnCl_2$ hydrosol) that adsorbs strongly onto the surface. The substrate and adsorbed catalyst should then be treated in an "accelerator bath", as is commonly known in the electroless plating art, using an acidic bath containing $PdCl_2$. Finally, thin support material 2 is plated in an electroless plating bath designed to deposit a thin layer of electrically conducting material 1 onto the surface of thin support material 2.

With electroplating, thin support material 2 is first activated using a commercial surface treatment (such as that available from Solution Technology Systems, Inc.). Thin support material 2 may then be electroplated in a manner well known to the electroplating industry with electrically conducting material 1, thereby forming metallized thin support substrate 3.

Metallized thin support material 3 is then laminated (e.g., by Litchfield Precision Components, Litchfield, Minn.) to first insulating substrate 4 (e.g., a bare fiberglass circuit board such as 10 mil thick FR4 from Norplex/Oak, La Crosse, Wis., available as product ED 130) using a suitable laminating adhesive system (e.g., Z-FLEX ™ adhesive system from Courtaulds Performance Films, Canoga Park, Calif.). First insulating substrate 4 could be any suitable non-conductive glass or plastic substrate with the desired supportive rigidity. In this step metallized thin support material 3 and first insulating substrate 4 could optionally be laminated using a hot press.

Once metallized thin support material 3 is supported on first insulating substrate 4, metallized thin support material 3 can be processed with a suitable solder resist to form an electrode area and a contact pad area for insertion into a meter and a power source. The surface of metallized thin support material 3 is cleaned with a suitable solvent system (e.g., a chlorofluorocarbon solvent) and coated with second insulating substrate 5, a commercial solder resist, either by screen printing or flood coating and then dried according to the manufacturer's specifications. An example of a commercial solder resist that could be used is ENPLATE ®DSR-3242 solder resist from Enthone-OMI, Inc. (a negative resist). The second insulating substrate 5 is exposed to ultra-violet light rays 7 through photomask 6. As a result, a latent image is generated in second insulating substrate 5 rendering it insoluble in a developer solution in those areas that were exposed to ultra-violet rays 7. Before developing, mask 6 is removed. The type of developer solution that should be used is process-dependent and generally will be specified by the manufacturer of the resist. Processing in the developer solution removes portions of second insulating substrate 5, thus forming first cutout portion 8 and second cutout portion 9. Following this procedure, the remaining second insulating substrate 5 may be permanently cured by a suitable combination of heat and ultra-violet light, making it a good barrier layer for applications in biological fluids. In addition to the negative solder resist described above, positive resists may also be used in accordance with the present invention. In the case of a positive solder resist, the resist used is insoluble in the developing solution, unless the resist is exposed to electromagnetic radiation as specified by the manufacturer of the resist.

As a result of the photolithographic process described above, first cutout portion 8 and second cutout portion 9 are formed in second insulating substrate 5, exposing the underlying metallized thin support material 3. In finished electrode element 11, the area of first cutout portion 8 defines the electrode area and second cutout portion 9 acts as a contact pad between electrode element 11 and a meter and a power source. When electrode element 11 is a reference electrode element, a reference electrode material (e.g., #DB2268 silver/silver chloride ink from Acheson Colloids Co., Port Huron, Mich.) is additionally applied to the electrode area defined by first cutout portion 8.

Importantly, although it is common when using photolithography to remove the resist layer, in the present invention second insulating substrate 5 is not removed and acts as an insulating substrate in the finished electrochemical sensor. In addition, vent port 10, which extends through second insulating substrate 5, metallized thin support material 3, and first insulating substrate 4, may be included and used as a vent port for the capillary space (described below) in the finished electrochemical sensor and/or as a means of introducing the sample to the capillary space. At this stage, any reagent that is required may be dispensed onto the appropriate electrode areas as described below.

As an alternative to applying the second insulating substrate and performing photolithography to define the working electrode area and contact pad as described above, a thin-film dielectric material may be screen printed onto metallized thin support material 3. The thin-film dielectric material may be UV-curable (e.g., #ML-25198 from Acheson Colloids or #5018 from DuPont Electronics) or heat-curable (e.g., #7192M from Metech). The thin-film dielectric material can be applied through a screen in a specific pattern so as to define first cutout portion 8 and second cutout portion 9 in the thin-film dielectric material, exposing the underlying metallized thin support material 3. In the finished electrode element, the area of first cutout portion 8 defines the electrode area and second cutout portion 9 acts as a contact pad between the electrode element and a meter and a power source. The thin-film dielectric material can be chosen such that it may be cross-linked photochemically after application to the metallized thin support material, thus increasing stability and adhesion to the surface of the metallized thin support material as well as forming an impenetrable barrier layer for use in biological media. The thin-film dielectric material also acts as an insulating substrate in the finished electrochemical sensor. A vent port may also be included and used as a means of introducing the sample in the finished electrochemical sensor as discussed above.

Figure 2:
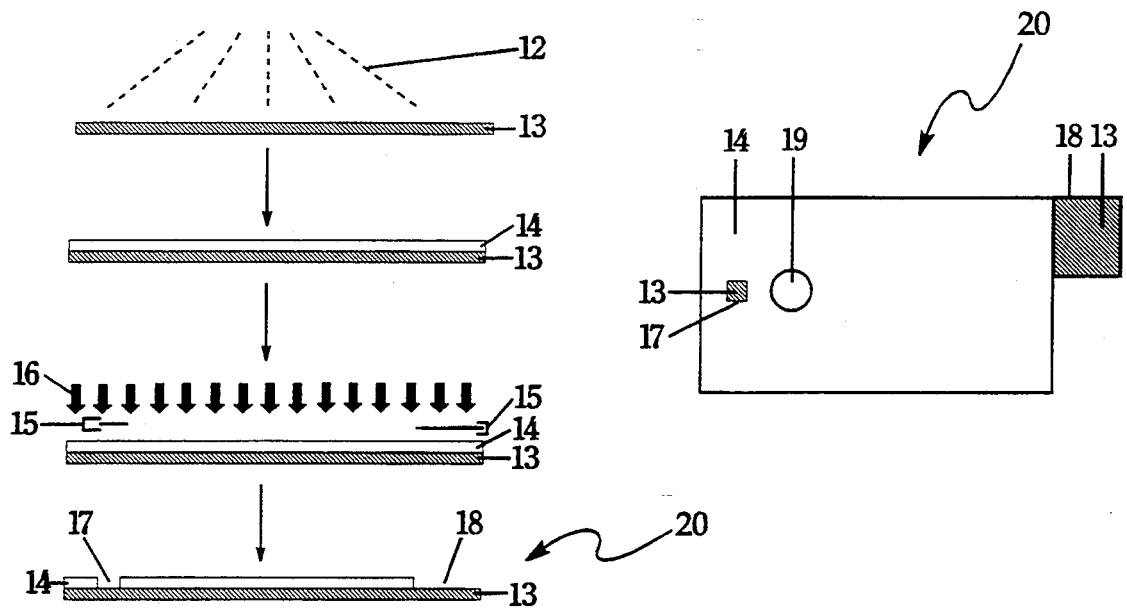
FIG. 2 shows another embodiment of a method of fabricating a working, counter, or reference electrode element in accordance with the present invention.

Another method that may be used to fabricate a working, counter, or reference electrode element in accordance with the present invention is shown in FIG. 2. In this embodiment, the electrically conducting material is deposited directly onto a more flexible first insulating substrate, thus facilitating a less-expensive, semi-continuous production method. Electrically conducting material 12 is vacuum sputtered or evaporatively deposited directly onto first insulating substrate 13 (e.g., by Courtaulds Performance Films, Canoga Park, Calif.). An example of a suitable substrate is MYLAR TM substrate (from DuPont) of approximately 10 mil thickness. Other suitable plastic, glass or fiberglass substrates may also be used. Alternatively, electroless or electroplating techniques as described above could be used to deposit metal 12 onto first insulating substrate 13.

Electrically conducting material 12 is then coated with second insulating substrate 14, such as a liquid negative solder resist (e.g., PROBOMER TM solder resist from Ciba-Geigy) via a flood or dip coating while still in a roll form and then dried using a suitable combination of infrared and thermal heating. Second insulating substrate 14 is exposed to ultra-violet light rays 16 through photomask 15. A latent image is generated in second insulating substrate 14 as described above and following removal of mask 15 and processing in the developer solution, portions of second insulating substrate 14 are removed forming first cutout portion 17 and second cutout portion 18. (As an alternative to the application of second insulating substrate 14, it is also possible to screen print a layer of dielectric ink in a specific pattern equivalent to that obtained via the exposure process disclosed above.) Second insulating substrate 14 may also be permanently cured as described above. In addition, solder resists other than described above (e.g., positive resists) may be used in accordance with the present invention.

In finished electrode element 20, the area of first cutout portion 17 defines the electrode area and second cutout portion 18 acts as a contact pad between electrode element 20 and a meter and a power source. As described above, when electrode element 20 is a reference electrode element, a reference electrode material (e.g., #DB2268 silver/silver chloride ink from Acheson Colloids Co., Port Huron, Mich.) is additionally applied to the electrode area defined by first cutout portion 17. Electrode element 20 may also include vent port 19.

The method described above for producing electrode elements utilizing a flexible first insulating substrate allows for a continuous production process, in which the metal is deposited on a roll of the first insulating substrate. The metallized plastic roll is then coated with the second insulating substrate and processed through an in-line exposure tool to expose a series of the desired patterns (electrode areas and contact pads) in the second insulating substrate along the roll. This is followed by a developing cycle, according to the manufacturer's specifications and familiar to those skilled in the art, followed by a curing cycle. This results in similarly exposed areas of metal for the electrode areas and the contact pad areas, although the array of multiple electrodes is supported on a continuous roll of plastic. Reagent is then dispensed onto the electrode areas defined in the second insulating substrate. An adhesive spacer layer (described below) is then applied via continuous roll lamination to the second insulating substrate (or dielectric ink). A second roll of electrodes is then fabricated as described above and laminated to the first roll so as to form a capillary chamber which exposes the active electrode areas as well as the reagent. The multiple sensors so defined on a continuous roll of material are then punched or die cut from the web prior to packaging.

As described above, a standard PCB substrate (a copper layer laminated to a fiberglass substrate) is inappropriate for use as a working electrode in an electrochemical sensor since it interferes with the electrochemical measurement. Specifically, when a mediator is being oxidized at the working electrode surface (anodic process), copper may also be oxidized and therefore interfere with the electrochemical measurement. However, when reduction is occurring at the surface of a reference or counter electrode (cathodic process), a standard PCB substrate may be used in the reference or counter electrode since copper will not be reduced and therefore will not interfere. One embodiment of a reference or counter electrode using a standard PCB as the first insulating substrate will now be described.

Figure 3:
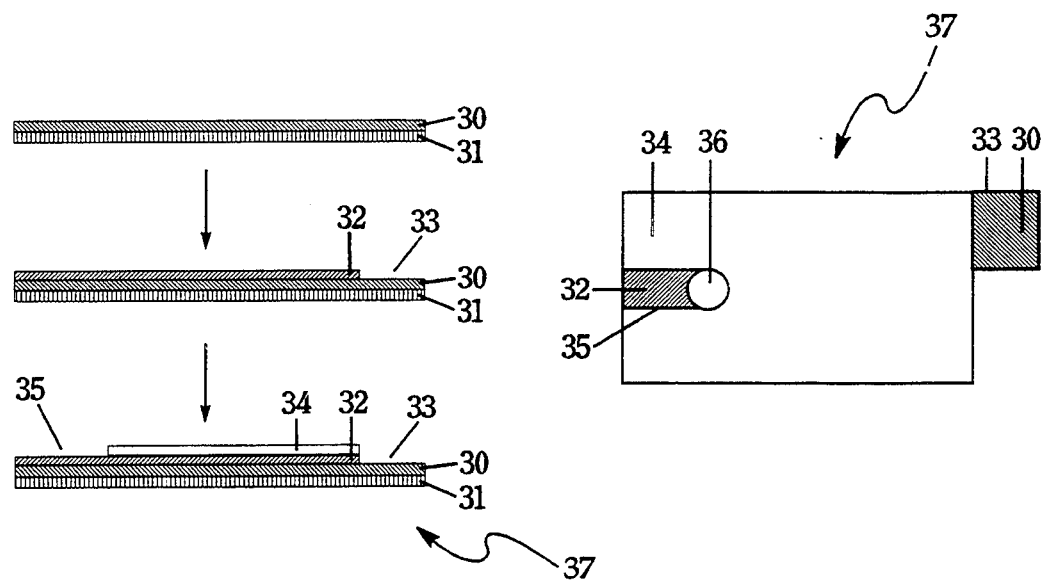
FIG. 3 shows a method of fabricating a reference or counter electrode element in accordance with the present invention.

Referring to FIG. 3, a standard PCB substrate, which includes copper layer 30 laminated to fiberglass substrate 31, is used as a first insulating substrate. Electrically conducting material 32 (e.g., #DB2268 silver/silver chloride ink from Acheson Colloids, Port Huron, Mich.) may be screen printed directly onto copper layer 30, leaving cutout portion 33 exposed. Finally, spacer 34 (e.g., MYLAR TM substrate with double-sided adhesive), which includes first cutout portion 35 and second cutout portion 33, is placed on top of electrically conducting material 32. Spacer 34 may also be any other suitable plastic or fiberglass. First cutout portion 35 and second cutout portion 33 may be cut out by using a laser process (e.g., by Laser Machining Inc., Somerset, Wis.). In finished reference or counter electrode element 37, the area of first cutout portion 35 exposes underlying electrically conducting material 32 and defines the reference or counter electrode area. Second cutout portion 33 exposes underlying copper layer 30 and acts as a contact pad between reference or counter electrode element 37 and a meter and a power source. In addition, vent port 36, which extends through spacer 34, electrically conducting material 32, copper layer 30, and fiberglass substrate 31, may be included and used as a vent port for the capillary space and/or as a means of introducing the sample to the capillary space as described above.

Figure 4:
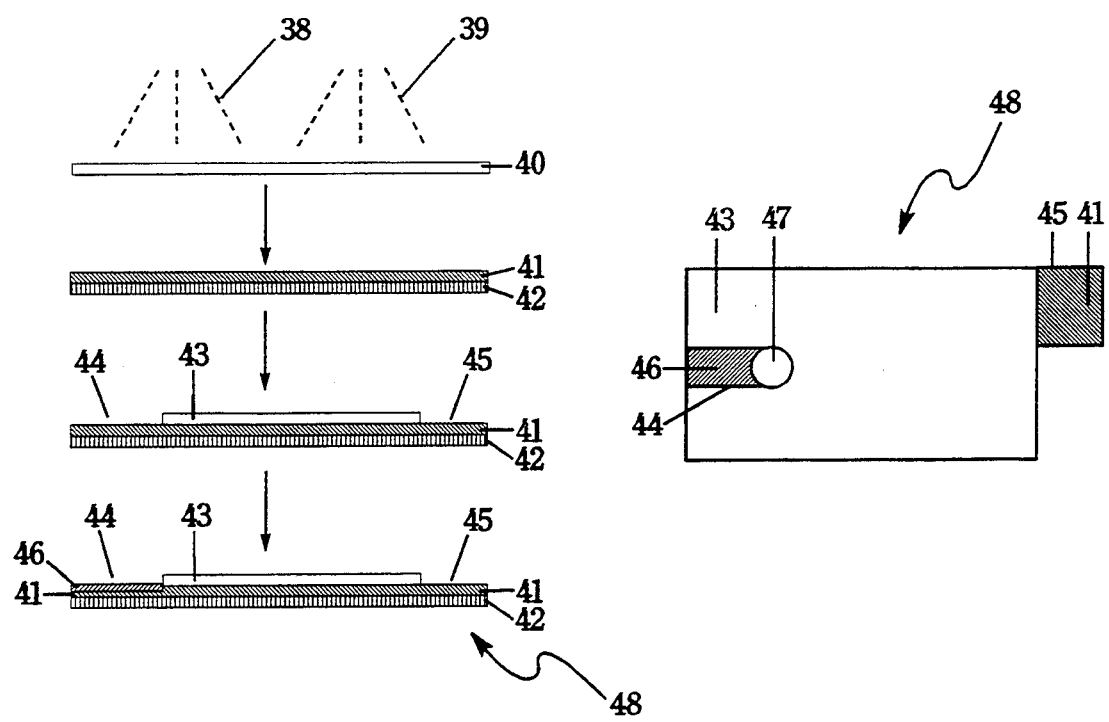
FIG. 4 shows another embodiment of a method of fabricating a reference or counter electrode element in accordance with the present invention.

Another method that may be used to fabricate a reference or counter electrode element in accordance with the present invention is shown in FIG. 4. A thin anchor or stabilizing layer of first electrically conducting material 38 (e.g., palladium) is sputtered or evaporatively deposited onto thin support material 40, followed by a thicker layer of second electrically conducting material 39 (e.g., silver), to form metallized thin support material 41 (e.g., by Courtaulds Performance Films, Canoga Park, Calif.). As described above, thin support material 40 may be a polyimide or other polymer such as polyester, PET, or polycarbonate. Metallized thin support material 41 may then be laminated to first insulating substrate 42, which may be fiberglass, glass, or plastic as described above. Alternatively, first electrically conducting material 38 may be directly sputtered or evaporatively deposited onto first insulating substrate 42 rather than onto thin support material 40. Spacer 43, which includes first cutout portion 44 and second cutout portion 45, is placed on top of metallized thin support material 41. Spacer 43 may be MYLAR TM substrate with double-sided adhesive as described above or any other suitable plastic or fiberglass. Finally, when second electrically conducting material 39 is silver, a solution of FeCl$_3$ (not shown) may be dispensed into first cutout portion 44 of spacer 43, where a layer of silver chloride 46 is formed by an oxidative process. The process of defining a reference electrode area can also optionally be assisted by applying and patterning a photoresist layer onto the surface of metallized thin support material 41 prior to treatment with FeCl$_3$. Alternatively, selected regions of metallized thin support material 41 may be dipped into solutions of FeCl$_3$ to achieve the same result. In finished reference or counter electrode element 48, the area of first cutout portion 44 exposes layer 46 and defines the reference or counter electrode area. Second cutout portion 45 exposes metallized thin support material 41 and acts as a contact pad between reference or counter electrode element 48 and a meter and a power source. In addition, vent port 47, which extends through spacer 43, metallized thin support material 41, and first insulating substrate 42, may be included and used as a means of introducing the sample in the finished electrochemical sensor as described above.

OPPOSING ELECTRODE ELECTROCHEMICAL SENSOR

Figure 5:
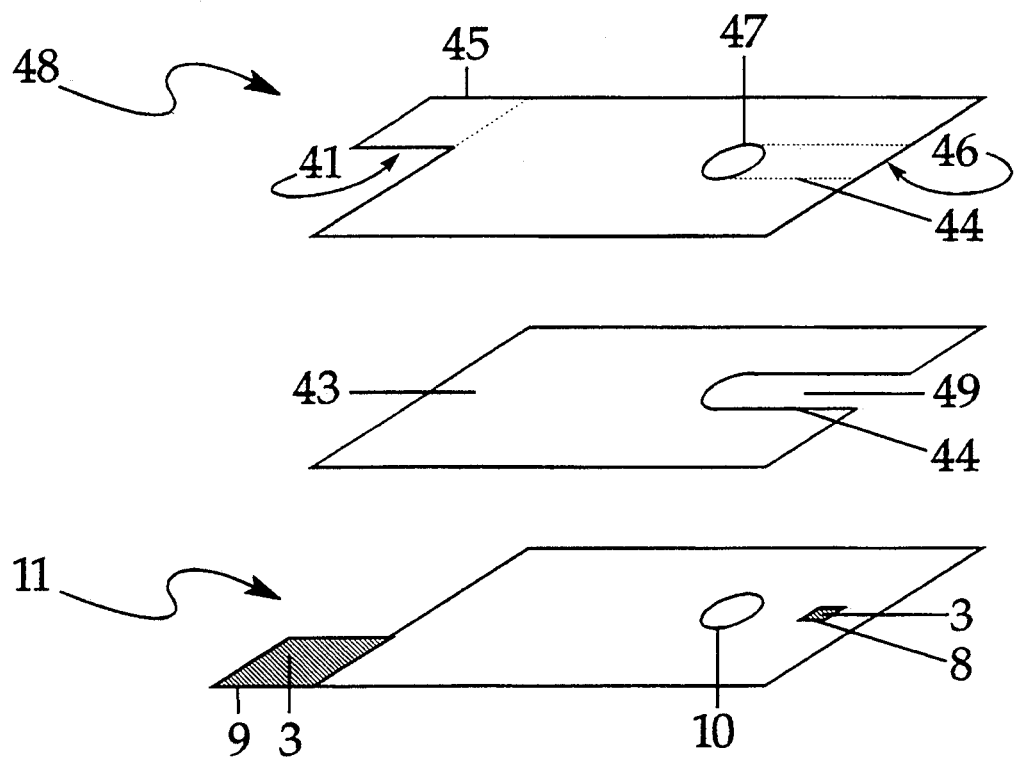
FIG. 5 shows an exploded view of the opposing electrode electrochemical sensor in accordance with the present invention.
Figure 6:
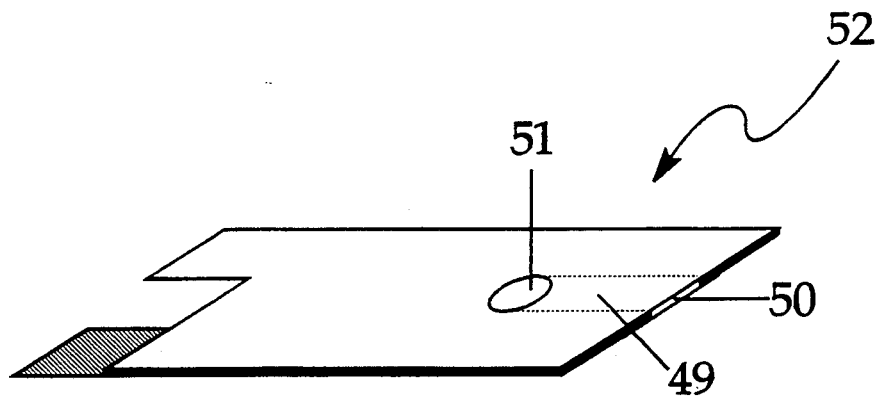
FIG. 6 shows an assembled view of the opposing electrode electrochemical sensor of FIG. 5.

One embodiment of an electrochemical sensor with an opposing electrode design in accordance with the present invention is shown in FIGS. 5 and 6. Reference or counter electrode element 48 is spatially displaced from working electrode element 11 by spacer 43. (Spacer 43 is normally affixed to reference or counter electrode element 48 during fabrication, but has been shown separate from element 48 for the purpose of FIG. 5.) First cutout portion 44 in spacer 43 forms capillary space 49 when situated between reference or counter electrode element 48 and working electrode element 11. First cutout portion 8 in working electrode element 11 exposes metallized thin support material 3, the working electrode area, which is exposed to the capillary space 49. First cutout portion 44 in spacer 43, when affixed to reference or counter electrode element 48, defines reference or counter electrode area 46 (shown in phantom lines in FIG. 5), which is also exposed to capillary space 49. Second cutout portions 9 and 45 expose metallized thin support materials 3 and 41 respectively and act as contact pads between electrochemical sensor 52 and a meter and a power source.

In assembled electrochemical sensor 52 shown in FIG. 6, capillary space 49 (shown in phantom lines) has first opening 50 at one edge of the electrochemical sensor. In addition, vent port 10 in working electrode element and/or vent port 47 in reference or counter electrode element 48 may be used to provide second opening 51 into capillary space 49. The vent port may optionally be used as a means of introducing the sample to the capillary space. In use, a sample containing an analyte to be detected or measured may be introduced into capillary space 49 of electrochemical sensor 52 through either opening 50 or vent port 51. In either case, the sample is spontaneously drawn into the electrochemical sensor by capillary action. (Preferably, a surfactant is included in the capillary space to aid in drawing the sample into the capillary space.) As a result, the electrochemical sensor automatically controls the sample volume measured without user intervention. In addition, since the sample is totally contained within capillary space 49, contamination of the meter into which electrochemical sensor 52 is inserted and the patient could be reduced or eliminated, a significant advantage when the sample is blood or a biological fluid.

FABRICATION OF ADJACENT ELECTRODE ELEMENTS FOR THE ADJACENT ELECTRODE ELECTROCHEMICAL SENSOR

Adjacent electrode elements may also be produced in accordance with the present invention to form an adjacent electrode electrochemical sensor as indicated in FIGS. 7 & 8. The process is similar to that described above for the opposing electrode elements. However, since the electrodes are on the same support substrate next to each other, an additional metal etching step is involved. Electrically conducting material 61 (e.g., a noble metal) is vacuum sputtered or evaporatively deposited onto thin support material 62 (e.g., polyimide or other polymer such as polyester, PET, or polycarbonate) to form metallized thin support material 63 as described above. (FIGS. 7a-7b.) This step may or may not be preceded by depositing a thin anchor layer. Alternatively, electrically conducting material 61 can be deposited onto the surface of thin support material 62 by the method of electroless plating or a combination of activation and electroplating as described above. Metallized thin support material 63 is then laminated to first insulating substrate 64 (e.g., a bare fiberglass circuit board such as 10 mil thick FR4) using a suitable laminating adhesive system (e.g., Z-FLEX TM adhesive system from Courtaulds Performance Films, Canoga Park, Calif.). (FIG. 7b.) First insulating substrate 64 could be any suitable non-conductive glass or plastic substrate as described above. In this step metallized thin support material 63 and first insulating substrate 64 could also be laminated using a hot press.

The surface of metallized thin support material 63 is then cleaned with a suitable solvent system and then coated with photoactive etch resist 65. (FIG. 7c.) Either positive or negative etch resists may be used. The coating method will depend on whether a semi-aqueous or liquid resist is used. The semi-aqueous resists are generally applied by a lamination process, whereas the liquid resists are dip-coated, spray-coated, curtain-coated, or screen printed. Specifically, in the case of a negative, semi-aqueous resist from DuPont, sold under the mark RESISTON, the resist is applied by a hot roll lamination process. Photoactive etch resist 65, metallized thin support material 63, and first insulating substrate 64 are then exposed to ultra-violet light 67 through photomask 66 and baked for 15 minutes at 180° F. (FIG. 7d.) As a result, a latent image is generated in photoactive etch resist 65 rendering it insoluble in a developer solution in those areas that were exposed to ultra-violet rays 67. Processing in the developer solution removes the unexposed areas of photoactive etch resist 65, thus exposing portions of underlying metallized thin support material 63. (FIG. 7e.)

The entire substrate is then placed in a bath containing a chemical etchant (e.g., when electrically conducting material 61 is gold, an aqua regia or a solution of KI and $I_2$ may be used) and incubated with constant stirring at a controlled temperature. The etchant dissolves the exposed metallized thin support material 63, but is unable to dissolve the portions of metallized thin support material 63 that are covered with photoactive etch resist 65. (FIG. 7f.) Photoactive etch resist 65 is then removed with a solvent revealing metallized thin support material 63 in the desired electrode pattern. (FIGS. 7g & 8a.) The electrode pattern may include, for example, contact pads 69, leads 70, and electrode areas 71. (FIG. 8a) Finally, leads 70 are insulated with second insulating substrate 68, which may be a solder resist or a screen printable dielectric as described above for the opposing electrode design. (FIGS. 7h & 8b.)

In accordance with the present invention, the counter electrode may then optionally be converted to a reference electrode by electroplating silver directly onto the counter electrode, followed by treatment with $FeCl_3$ to convert the silver surface to silver chloride. To facilitate this process a sacrificial interconnecting bus could be designed into the layout to allow multiple electrodes to be electroplated in one step. The other areas of metal would need to be protected during the plating step since it is generally done as a batch process. This could be accomplished with an etch resist in a manner similar to that described above for the adjacent working/counter electrode arrangement. Alternatively, a layer of reference electrode material (e.g., silver chloride ink) may be screen printed on top of the metal layer to yield a reference electrode.

REAGENT

Many different types reagents may be applied to the working electrode and/or the reference or counter electrode to provide for a fully functional sensor whose signal is selective for and sensitive to the concentration of an analyte (e.g., glucose). These reagents can be dispensed onto the working electrode area of the electrochemical sensors described above using an automated mechanical dispenser, screen printing, slot or roll coating, spin coating, blade coating, or inkjet printing. (Sometimes, both working and counter electrode areas will be coated with a reagent.) The reagents thus dispensed form a thin coating over the electrode which is rapidly swollen upon application of the sample (e.g., blood), at which time a suitable potential may be applied to the electrodes and a current measurement made. The current measurement may then be related to the concentration of the target analyte in the sample. The use of polymeric materials and a capillary chamber to contain the reagent greatly reduces the risk of contamination by chemicals in the sensor of the open wound in the patient's finger.

An example of a reagent that may be used with the present invention for the detection of glucose in a whole blood sample, designed to be used with the opposing electrode electrochemical sensor having a working electrode element and a reference electrode element, will now be described. The components of the reagent are listed below in table 1.

TABLE 1

| reagent components | |
|---|---|
| Component | Amount |
| 2-(N-morpholino) ethanesulphonic acid (MES Buffer) | 100 millimolar (mM) |
| Triton X-100 | 0.08% wt/wt |
| Polyvinyl alcohol (PVA), mol. weight 10K, 88% hydrolyzed | 1.00% wt/wt |
| Imidazole osmium mediator (reduced form - synthesis described below) | 6.2 mM |
| Glucose Oxidase | 6000 units/ml |

Following is a description of how the reduced form of the imidazole osmium mediator was synthesized. The osmium intermediate $(Os(bpy)_2Cl_2)$ was first synthesized, followed by the reduced form of the imidazole osmium mediator $[Os(II)(bpy)_2(im)Cl]+[Cl]-$. ("bpy" is a shorthand abbreviation for 2-2'-bipyridine and "im" is a shorthand abbreviation for imidazole.)

SYNTHESIS OF OSMIUM INTERMEDIATE 1) 19.335 g $K_2OsCl_6$ (0.04019 mole—from Aldrich) and 13.295 g bpy (0.08512 mole—from Aldrich) were weighed and transferred into a 1000 ml 1-neck flask.

2) 400 ml N,N'-dimethylformamide (DMF—from Mallinckrodt) was added to the flask to dissolve all reactants.

3) The flask contents were heated to reflux (152°–54° C.) with stirring. Reflux was maintained for 1 hour with lower heat (setting was decreased from 100% to 65% on variable transformer) to avoid overboiling.

4) The heat was turned off and the flask was cooled with continued stirring to 30°–40° C. in 1–2 hours.

5) The mixture was filtered with vacuum using a medium grade glass fritted filter (150 ml).

6) The flask was rinsed with 20 ml DMF and poured into the filter.

7) The filtered DMF solution was transferred to a 3 liter (l) beaker.

8) 22.799 grams $Na_2S_2O_4$ (from Mallinckrodt) was weighed and transferred to a separate 2 l beaker.

9) 2 l deionized water was added to the beaker to dissolve the $Na_2S_2O_4$.

10) The $Na_2S_2O_4$ aqueous solution was transferred to a dropping funnel and added dropwise (about 5 drops/second), over a period of 45 minutes, to the stirring DMF solution.

11) The mixture was cooled in an ice bath for more than 3 hours.

12) The cooled mixture was filtered with vacuum using Whatman qualitative filter paper in a ceramic filter.

13) The filtered product was washed twice with 50 ml $H_2O$; twice with 50 ml methanol; and twice with 50 ml diethyl ether.

14) The product, $Os(bpy)_2Cl_2$, was dried under high vacuum (about 30 in. Hg) at 50° C. for more than 15 hours (overnight).

15) The product was weighed, transferred to a brown bottle having a screw-on cap, and stored in desiccator at room temperature. Yield: theoretical=23.35 g, actual=15.56 g, yield=66.6%.

SYNTHESIS OF THE REDUCED FORM OF THE IMIDAZOLE OSMIUM MEDIATOR 1) 14.01 g $Os(bpy)_2Cl_2$ (0.0244 mole) and 2.30 g imidazole (0.0338 mole—from Aldrich) were weighed and transferred into a 2000 ml 1-neck flask.

2) 600 ml ethanol and 600 ml deionized water were added to dissolve all reactants.

3) The flask contents were heated to reflux with stirring and reflux was maintained for 6 hours with lower heat (setting was decreased from 90% to 60% on variable transformer) to avoid overboiling.

4) The heat was turned off and the flask cooled with continued stirring to 30°–40° C. over a period of 1 hour.

5) Half of the solution was transferred to a 1000 ml 1-neck flask and the solvents were rotary evaporated. The remainder of the solution was added to the flask and the solvents were rotary evaporated.

6) The dried product was rinsed on the flask wall with 50 ml ether and the ether wash was discarded.

7) The product was dried under high vacuum (about 30 in. Hg) at 50° C. for more than 15 hours (overnight).

8) The flask wall was scraped to collect the product, $[Os(II)(bpy)_2(im)Cl]^+[Cl]^-$. The product was weighed and transferred to a brown bottle having a screw-on cap. The bottle was stored in a desiccator at room temperature. Yield: theoretical=16.3 g, actual=16.1 g, yield=98.8%.

Following is a description of how the reagent described in table 1 was prepared and used in combination with opposing electrode elements to form an electrochemical sensor.

1) Polymer matrix a) 1.952 g MES buffer was added to 85 ml nanograde water. The mixture was stirred until dissolved. The pH of the solution was adjusted to 5.5 with NaOH and the total volume of the solution was brought to 100 ml.

b) 0.08 g of Triton X-100 and 1 g of PVA was added to a 150 ml beaker. Buffer solution was added to bring the total weight of the solution to 100 g. The mixture was then heated to boiling to dissolve the PVA.

2) Coating mixture a) 4.0 mg of the reduced osmium mediator, $[Os(II)(bpy)_2(im)Cl]^+[Cl]^-$, was added to 1 ml of the polymer matrix. The mixture was vortexed to dissolve the mediator. 6000 units of glucose oxidase was added to the mixture and the solution was mixed until the enzyme was dissolved.

Although the reagent described above is preferred for use with this invention, other types of reagents, which are specifically reactive with an analyte in a fluid sample to produce an electrochemically-measurable signal which can be correlated to the concentration of the analyte in the fluid sample, may be used. The reagent should include at least a mediator and an enzyme. Preferably, the reagent should also includes a buffer, a film former, and a surfactant as described above.

Other redox mediator systems could also be utilized (e.g., using potassium ferricyanide as the redox mediator rather than the imidazole osmium mediator described above) as well as redox polymer systems (in which the mediator and enzyme are immobilized on the electrode surface).

USE OF THE ELECTROCHEMICAL SENSOR

The electrochemical sensor described above may be used for, but is not limited to, the determination of blood glucose levels using a small drop of blood (3–20 $\mu$l) obtained from the patient's finger or other location by the use of a lancing device. A significant advantage to the present invention is the low volume required for the measurement, thus allowing for a very low pain lancet device which produces low sample volumes.

An example of how an opposing electrode electrochemical sensor was made and used to determine the concentration of glucose in a whole blood sample will now be described. A reference electrode element was fabricated as described above, having gold as the electrically conducting material and having a spacer attached to expose a portion of the gold (capillary space). A silver/silver chloride polymer thick film ink (Acheson Colloids DB 2286) was thinned 2:1 wt/wt with butoxyethanol. 2.5 $\mu$l of the resulting mixture was applied to the capillary space and spread to fill the capillary area. The electrode was then dried for 15 minutes at 90° C.

A working electrode element was fabricated as described above, having gold as the electrically conducting material. 1 $\mu$l of the coating mixture (from the reagent example described above) was then applied to the working electrode surface of the working electrode element. The coated electrode was dried at 45° C. for 15 minutes.

Figure 9:
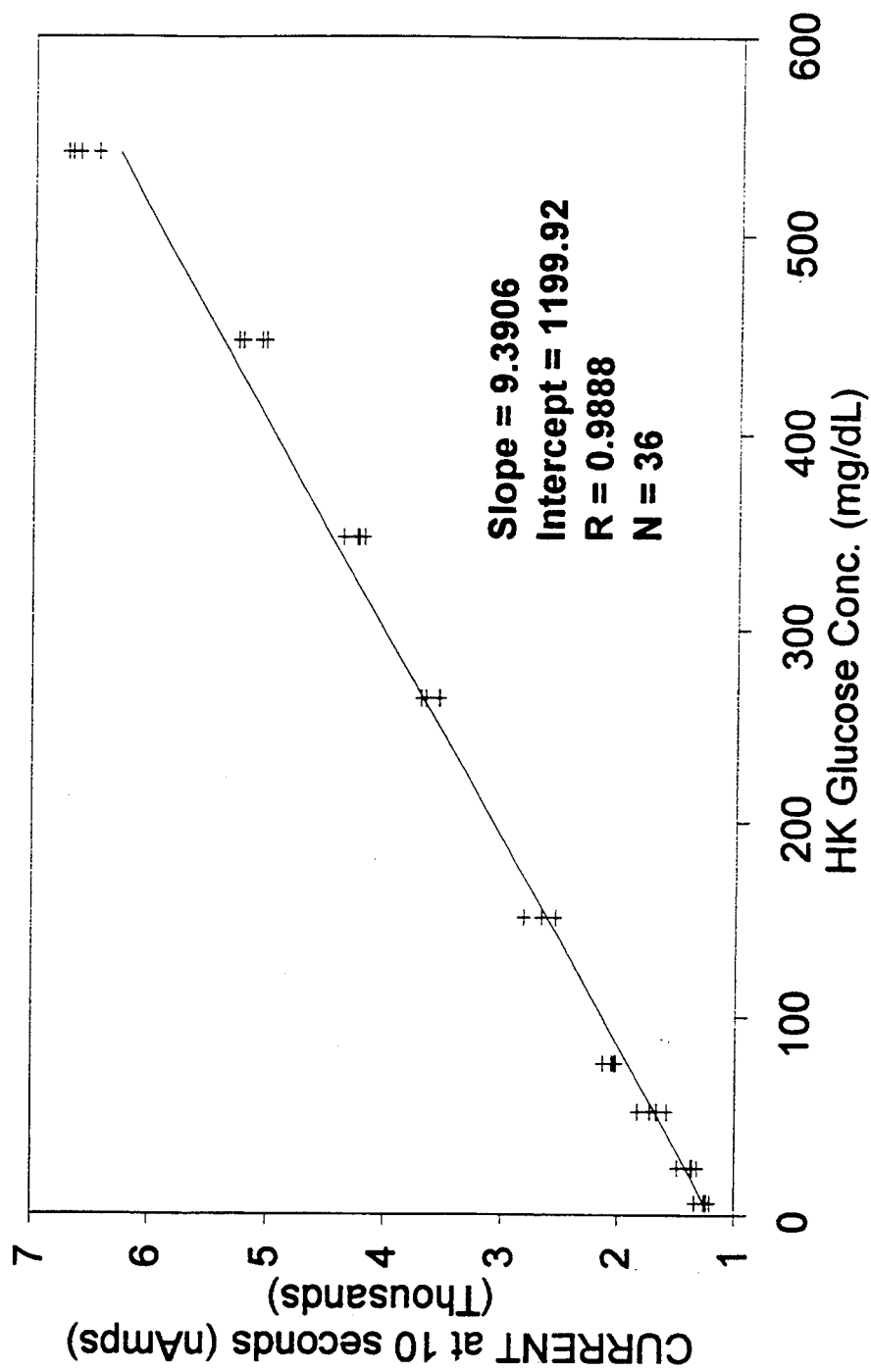
FIG. 9 shows a dose response of one embodiment of a electrochemical sensor in accordance with the present invention.

The working electrode element was then "sandwiched" together with the reference electrode element as described above and as illustrated in FIGS. 5 & 6 to form the completed electrochemical sensor. The completed electrochemical sensor was used, as described below, to perform a glucose assay. The working electrode potential was made +200 millivolts (mv) versus the Ag/AgCl reference electrode by a potentiostat. 10 μl of spiked glycolyzed venous blood was added to capillary space 49 through first opening 50. Current was measured 10 seconds after applying the sample to the electrochemical sensor. FIG. 9 shows a dose response curve generated by the assay of spiked glycolyzed venous blood samples with different levels of glucose.

It is intended that an electrochemical sensor made in accordance with the present invention should be inserted into a small meter device where the contact tabs can make electrical contact with the measuring circuit within the meter. The meter will normally be adapted to apply an algorithm to the current measurement, whereby the analyte level is provided and visually displayed. Examples of improvements in such a power source and meter are the subject of commonly assigned U.S. Pat. No. 4,963,814—"Regulated Bifurcated Power Supply" (Parks et al., issued Oct. 16, 1990), U.S. Pat. No. 4,999,632—"Analog to Digital Conversion with Noise Reduction" (Parks, issued Mar. 12, 1991), U.S. Pat. No. 4,999,582—"Electrochemical sensor Electrode Excitation Circuit" (Parks et al., issued Mar. 12, 1991), and U.S. Pat. No. 5,243,516—"Biosensing Instrument and Method" (White, issued Sep. 7, 1993), the disclosures of which are hereby incorporated by reference.

The present invention has been disclosed in the above teachings and drawings with sufficient clarity and conciseness to enable one skilled in the art to make and use the invention, to know the best mode for carrying out the invention, and to distinguish it from other inventions and from what is old. Many variations and obvious adaptations of the invention will readily come to mind, and these are intended to be contained within the scope of the invention as claimed below.

What is claimed is:

1. An electrochemical sensor useful for measuring the concentration of an analyte in a fluid sample, comprising:
   (a) opposing working and counter electrode elements, spatially displaced by a spacer having a first cutout portion forming a capillary space between the working and counter electrode elements and a second cutout portion allowing electrical connection between the counter electrode element and a meter and power source, wherein the capillary space is vented by a port in the working or counter electrode elements, the working electrode element including
   1) a first insulating substrate,
   2) an electrically conducting material affixed to the first insulating substrate, and
   3) a second insulating substrate affixed to the electrically conducting material and the spacer, the second insulating substrate having a first cutout portion for exposing a portion of the electrically conducting material to the capillary space and a second cutout portion which allows contact between the electrically conducting material and the meter and power source,
   the counter electrode element including
   1) an insulating substrate, and
   2) an electrically conducting material affixed to the insulating substrate and the spacer; and
   (b) a reagent disposed in the capillary space, the reagent being specifically reactive with the analyte in the fluid sample to produce an electrochemically-measurable signal which can be correlated to the concentration of the analyte in the fluid sample.

2. The electrochemical sensor of claim 1, wherein the vent port extends through the working electrode element and the counter electrode element.

3. The electrochemical sensor of claim 2, wherein the counter electrode element further comprises:
   3) a second insulating substrate affixed to the electrically conducting material and the spacer, the second insulating substrate having a first cutout portion for exposing a portion of the electrically conducting material to the capillary space and a second cutout portion which overlays the second cutout portion of the spacer.

4. The electrochemical sensor of claim 3, wherein the electrically conducting material of the working electrode element is a noble metal or carbon.

5. The electrochemical sensor of claim 4, wherein the electrically conducting material of the counter electrode element is a noble metal or carbon.

6. The electrochemical sensor of claim 5, wherein the second insulating substrate is a solder resist.

7. The electrochemical sensor of claim 6, further comprising:
   (d) the power source in electrical connection with the working and counter electrode elements; and
   (e) the meter in electrical connection with the working and counter electrode elements and capable of measuring current.

8. The electrochemical sensor of claim 7, wherein the reagent comprises a mediator and an enzyme.

9. The electrochemical sensor of claim 8, wherein the reagent further comprises a buffer, a film former, and a surfactant.

10. The electrochemical sensor of claim 9, wherein the analyte is glucose, the mediator is $[Os(II)(bpy)_2(im)Cl]^+[Cl]^-$, the enzyme is glucose oxidase, the buffer is MES buffer, the film former is polyvinyl alcohol, and the surfactant is a nonionic surfactant.

11. The electrochemical sensor of claim 8, wherein the mediator is $Os(II)(bpy)_2(im)Cl]^+[Cl]^-$ and the enzyme is glucose oxidase.

12. An electrochemical sensor useful for measuring the concentration of an analyte in a fluid sample, comprising:
   (a) opposing working and reference electrode elements, spatially displaced by a spacer having a first cutout portion forming a capillary space between the working and reference electrode elements and a second cutout portion allowing electrical connection between the reference electrode element and a meter and power source, wherein the capillary space is vented by a port in the working or reference electrode elements, the working electrode element including
   1) a first insulating substrate,
   2) an electrically conducting material affixed to the first insulating substrate, and
   3) a second insulating substrate affixed to the electrically conducting material and the spacer, the second insulating substrate having a first cutout portion for exposing a portion of the electrically conducting material to the capillary space and a second cutout portion which allows contact between the electrically conducting material and the meter and power source,
   the reference electrode element including
   1) an insulating substrate, 2) an electrically conducting reference material affixed to the insulating substrate and the spacer; and (b) a reagent disposed in the capillary space, the reagent being specifically reactive with the analyte in the fluid sample to produce an electrochemically-measurable signal which can be correlated to the concentration of the analyte in the fluid sample.

13. The electrochemical sensor of claim 12, wherein the vent port extends through the working electrode element and the reference electrode element.

14. The electrochemical sensor of claim 13, wherein the reference electrode element further comprises:

4) a second insulating substrate affixed to the reference electrode material and the spacer, the second insulating substrate having a first cutout portion for exposing a portion of the electrically conducting material to the capillary space and a second cutout portion which overlays the second cutout portion of the spacer.

15. The electrochemical sensor of claim 14, wherein the electrically conducting material of the working electrode element is a noble metal or carbon.

16. The electrochemical sensor of claim 15, wherein the electrically conducting reference material of the reference electrode element is silver/silver chloride.

17. The electrochemical sensor of claim 16, wherein the second insulating substrate is a solder resist.

18. The electrochemical sensor of claim 17, further comprising:

(d) the power source in electrical connection with the working and reference electrode elements; and (e) the meter in electrical connection with the working and reference electrode elements and capable of measuring current.

19. The electrochemical sensor of claim 18, wherein the reagent comprises a redox mediator and an enzyme.

20. The electrochemical sensor of claim 19, wherein the reagent further comprises a buffer, a film former, and a surfactant.

21. The electrochemical sensor of claim 20, wherein the analyte is glucose, the redox mediator is $[Os(II)(bpy)_2(im)Cl]^+[Cl]^-$, the enzyme is glucose oxidase, the buffer is MES buffer, the film former is polyvinyl alcohol, and the surfactant is a nonionic surfactant.

22. The electrochemical sensor of claim 19, wherein the redox mediator is $[Os(II)(bpy)_2(im)Cl]^+[Cl]^-$ and the enzyme is glucose oxidase.

* * * * *